United States Patent [19]

Crainich

[11] Patent Number: 5,507,727
[45] Date of Patent: Apr. 16, 1996

[54] INFLATION DEFLATION SYRINGE ASSEMBLY FOR USE IN ANGIOPLASTY PROCEDURES

[75] Inventor: Lawrence Crainich, Charlestown, N.H.

[73] Assignee: Design Standards Corporation, Charlestown, N.H.

[21] Appl. No.: 284,310

[22] Filed: Aug. 2, 1994

[51] Int. Cl.⁶ .............................. A61M 29/00; A61M 5/00
[52] U.S. Cl. .................................. 604/97; 604/209; 604/99
[58] Field of Search .............................. 604/97–100, 121, 604/208, 209, 211, 224, 227

[56] References Cited

U.S. PATENT DOCUMENTS

| | | | |
|---|---|---|---|
| 2,632,445 | 3/1953 | Kas, Sr. | 604/209 |
| 3,110,310 | 11/1963 | Cislak | 604/209 |
| 3,517,668 | 6/1970 | Brickson | 604/209 |
| 4,370,982 | 2/1983 | Reilly | 604/98 |
| 4,589,870 | 5/1986 | Citrin et al. | 604/210 |
| 4,832,692 | 5/1989 | Box et al. | |
| 4,940,459 | 7/1990 | Noce | 604/98 |
| 4,994,065 | 2/1991 | Gibbs et al. | 606/92 |
| 5,137,514 | 8/1992 | Ryan. | |
| 5,168,757 | 12/1992 | Rabenau et al. | 73/714 |
| 5,209,731 | 5/1993 | Sterman et al. | 604/97 |
| 5,209,732 | 5/1993 | Lampropoulos et al. | 604/99 |
| 5,306,248 | 4/1994 | Barrington | 604/97 |

*Primary Examiner*—C. Fred Rosenbaum
*Assistant Examiner*—Adam J. Cermak
*Attorney, Agent, or Firm*—Bachman & LaPointe

[57] ABSTRACT

This invention relates to a syringe assembly which includes a housing having a barrel having a forward fluid discharge end; a plunger disposed within said barrel and having a threaded rod extending therefrom; a threaded nut element for engaging said threaded rod for threaded advancement of said plunger relative to said barrel; and a control lever for positively engaging and positively disengaging said threaded nut element with said threaded rod, said control lever having a first arm member connected to said threaded nut element and being pivotably mounted for pivot between an engaged position wherein said first arm member positively engages said threaded nut element with said threaded rod, and a disengaged position wherein said first arm member positively disengages said threaded nut element from said threaded rod.

18 Claims, 2 Drawing Sheets

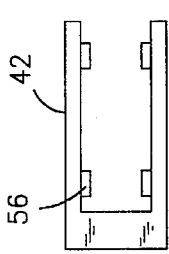
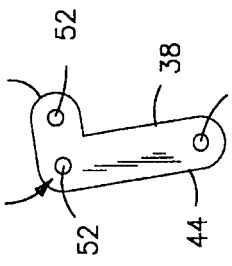
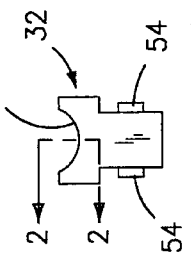
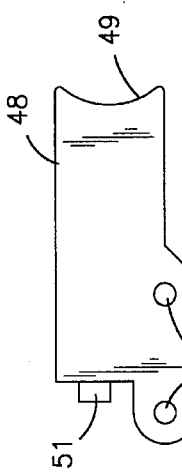
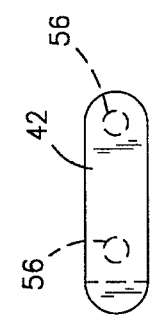
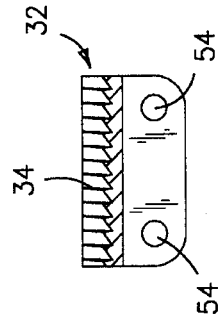
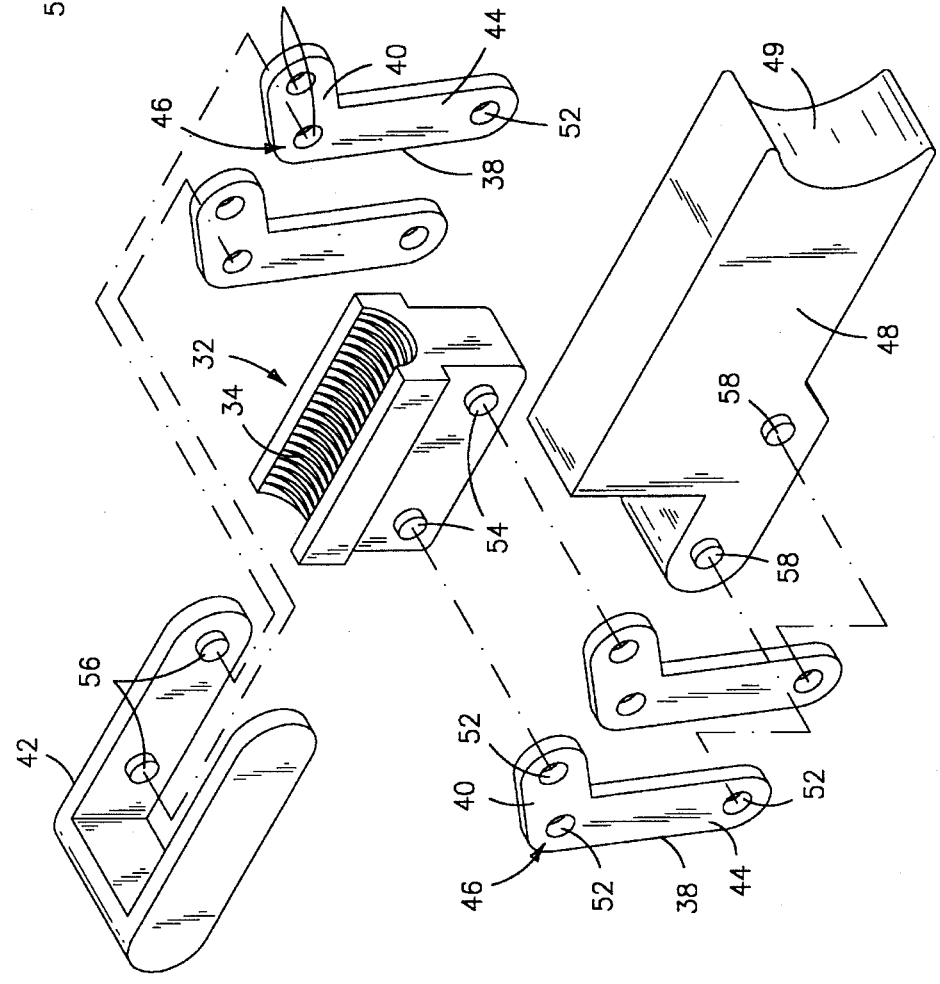

INFLATION DEFLATION SYRINGE ASSEMBLY FOR USE IN ANGIOPLASTY PROCEDURES

BACKGROUND OF THE INVENTION

The invention relates to a syringe assembly for an inflation syringe for inflating and for rapidly deflating an angioplasty balloon component of a catheter to which the syringe assembly is attached.

Numerous patents exists which disclose such syringe assemblies including U.S. Pat. No. 4,832,692 to Box et al., and U.S. Pat. No. 5,137,514 to Ryan.

The above patents represent useful advances in the art. Both present disclosures which partially address problems which have existed in the art. Nevertheless, the need still exists for a syringe assembly wherein the plunger for pressurizing the balloon catheter is reliably engaged and disengaged for advance and release within the syringe as desired.

It is therefore the primary object of the present invention to provide a syringe assembly wherein the plunger member is reliably and securely engaged and advanced when desired, and is also rapidly disengagable and re-engageable when needed.

It is a further object of the present invention to provide a syringe assembly wherein advancement of the plunger member may be accomplished through a direct forward ratcheting advance of the plunger as well as the conventional threaded advance of the plunger.

It is a still further object of the present invention to provide a syringe assembly which is capable of providing a front and back pulsation or vibration of the plunger member so as to pulse the balloon catheter to which the syringe assembly is attached as desired.

Other objects and advantages will appear hereinbelow.

SUMMARY OF THE INVENTION

In accordance with the present invention, the foregoing objects and advantages are readily attained.

In accordance with the invention, a syringe assembly is provided which comprises a housing having a barrel having a forward fluid discharge end; a plunger disposed within said barrel and having a threaded rod extending therefrom; threaded means for engaging said threaded rod for threaded advancement of said plunger relative to said barrel; and control means for positively engaging and positively disengaging said threaded means with said threaded rod, said control means having a first arm member connected to said threaded means and being pivotably mounted for pivot between an engaged position wherein said first arm member positively engages said threaded means with said threaded rod, and a disengaged position wherein said first arm member positively disengages said threaded means from said threaded rod.

In further accordance with the invention, the syringe assembly may be provided with pulsing means for pulsing said plunger in said barrel between a starting position and a forward pulsed position wherein said plunger is displaced forwardly from said starting position.

In accordance with the foregoing, a syringe assembly is provided wherein the threaded means for the plunger, when engaged, is both positively and securely engaged against rearward slippage, and is also forwardly ratchetable as desired. Furthermore, in accordance with an alternate embodiment of the invention, additional means are provided for pulsing the plunger forward and backward in the barrel of the housing for providing a pulsation of fluid delivered from the syringe assembly to a balloon catheter.

BRIEF DESCRIPTION OF THE DRAWINGS

A detailed description of preferred embodiments of the invention follows, with reference to the attached drawings wherein:

FIG. 2 is a partially sectional view of a half-nut element of the advancing structure of a syringe assembly in accordance with the invention;

FIG. 3 is an end view of the half-nut member of FIG. 2;

FIG. 4 is a side view of a lever component of a syringe assembly according to the invention;

FIG. 5 is a top view of a carriage member of a syringe assembly according to the invention;

FIG. 6 is a side view of the carriage member of FIG. 5;

FIG. 7 is a side elevational view of a trigger member of a syringe assembly according to the invention; and FIG. 8 is an exploded view of the trigger and related assemblies which are illustrated individually in FIGS. 2–7.

DETAILED DESCRIPTION

Figure 1:
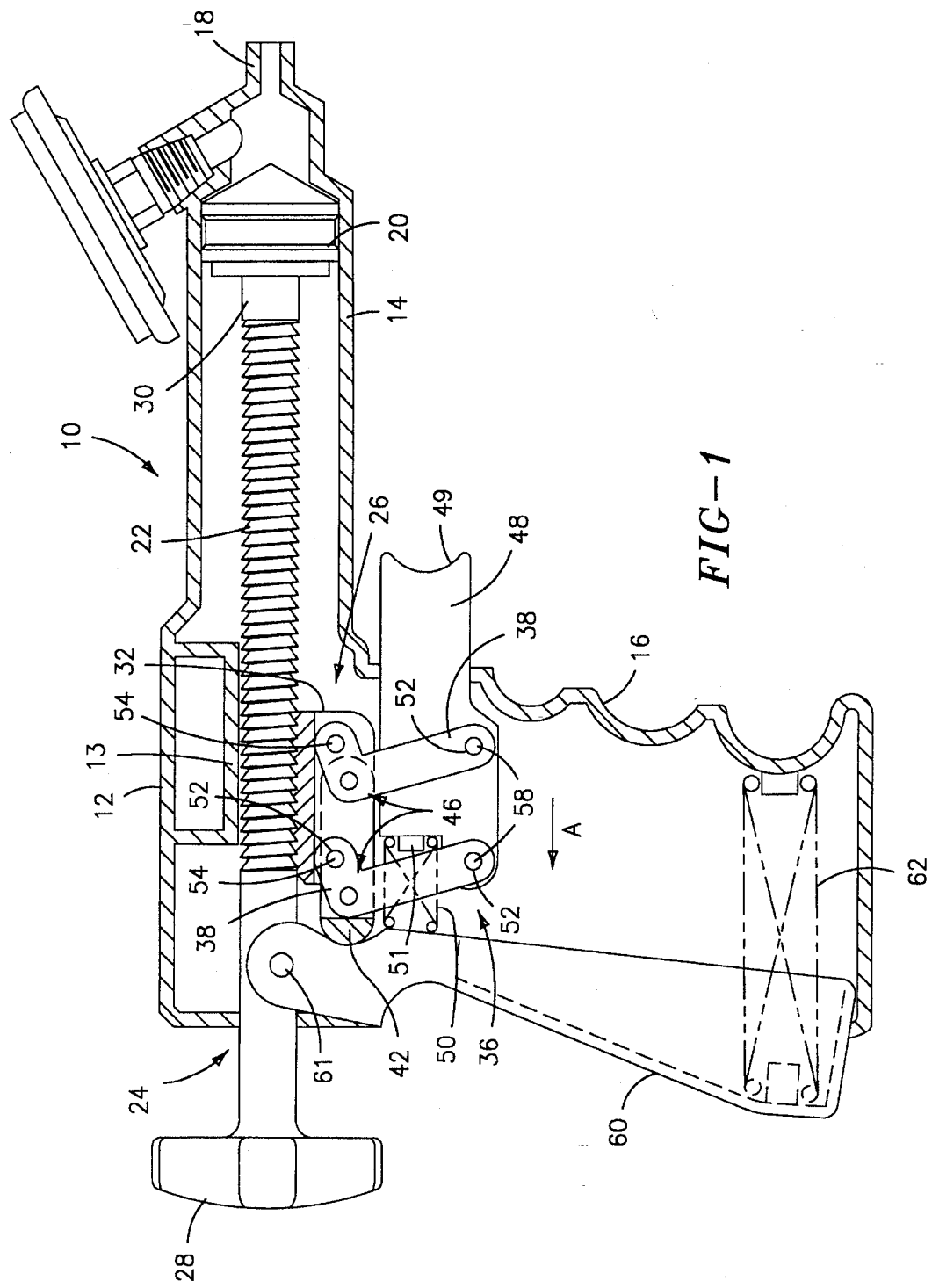
FIG. 1 is a cross section of a syringe assembly in accordance with the invention.

The invention relates to a syringe assembly having a plunger disposed in a barrel for discharging fluid to a balloon catheter. In accordance with the invention, the plunger is disposed in the barrel so as to provide enhanced resistance against rearward slippage and further so as to provide advancement of the plunger member either by ratcheting forward, or by conventional threaded advancement.

FIG. 1 illustrates a cross section of a syringe assembly 10 in accordance with the invention. Syringe assembly 10 preferably includes a housing 12 having a barrel portion 14, and a downwardly depending pistol grip 16. Barrel 14 preferably has an outlet 18 through which fluid is delivered for example via a hose (not shown) to a balloon catheter (also not shown) which is to be inflated as part of a medical or surgical operation. In accordance with the invention, a plunger 20 is disposed within barrel 14 for movement within barrel 14 so as to pressurize fluid contained within barrel 14 and to discharge fluid through outlet 18 and thereby pressurize and inflate a balloon catheter or other device which may be attached to syringe assembly 10. Plunger 20 is preferably mounted on a structure for advancement in barrel 14 so as to provide secure and reliable advancement of plunger 20 within barrel 14 in a manner wherein backward slippage of plunger 20, for example due to high pressure in the balloon catheter and housing to the pressure side of plunger 20, is substantially prevented.

In accordance with the invention, plunger 20 may be positioned at the end of a threaded rod 22 which preferably extends outside of housing 12 at a rear end 24 thereof. Rod 22 is preferably threaded and is releasably engaged by a threaded member 26 so that rotation of rod 22, for example via knob 28, advances and retreats plunger 20 within and relative to barrel 14 depending upon the direction of rotation of rod 22. Housing 12 may preferably be provided with a support 13 positioned relative to rod 22 so as to support and hold rod 22 securely in place. Plunger 20 is preferably rotatably mounted on the end 30 of rod 22 so that rotation of rod 22 is not transmitted to plunger 20.

Syringe assembly 10 is generally used as follows. Syringe assembly 10 is connected via a hose or conduit to a balloon catheter positioned at a point of treatment. Once properly connected, rotation of knob 28 serves to advance plunger 20 toward outlet 18 of barrel 14 so as to pressurize fluid contained in the barrel 14/hose/balloon catheter circuit. This causes inflation of the balloon catheter as desired.

It is desirable to provide structure for rapidly disengaging threaded member 26 from rod 22 so as to release pressure from the balloon catheter or other device on which syringe assembly 10 is being used. In accordance with the invention, threaded engagement member 26 is preferably rapidly disengagable from rod 22 so that rod 22 is free to retreat in barrel 14 and pressure in the balloon catheter may be released if necessary in the case of an emergency or upon completion of the desired procedure. In accordance with the foregoing, positive engagement and disengagement of threaded member 26 with rod 22 is provided. FIGS. 2–7 illustrate various elements of the assembly used for advancing plunger 20 and for engaging and disengaging threaded member 26 with rod 22. FIG. 8 illustrates an exploded view of this entire assembly for further clarity.

Referring to FIGS. 2 and 3, threaded member 26 preferably comprises a substantially half-nut member 32 having a threaded portion 34 matching the thread of rod 22 so as to firmly engage therewith. In accordance with the invention, and also as shown in the cut-away portion of FIG. 1, threads of rod 22 and half-nut 32 are preferably so-called buttress type threads. In other words, the threads of rod 22 are preferably deflected rearwardly, while threads of half-nut member 32 are preferably deflected forwardly. In this manner, pressure exerted against plunger 20 and rod 22 causes a more positive engagement of threads between rod 22 and half-nut 32. Thus, plunger 20 is securely held against rearward slippage. Further, the angle of threads of rod 22 and half-nut member 32 makes it possible to forwardly ratchet rod 22 relative to half-nut 32 without exerting excessive force on knob 28. Also, secure engagement between rod 22 and half-nut 32 is maintained so that rod 22 may be released after being ratcheted to the desired position without fear that rod 22 and half-nut 32 are not properly engaged.

In accordance with the invention, half-nut 32 is positively engaged and disengaged with rod 22 through a lever structure 36. Lever structure 36 preferably includes levers 38 pivotably mounted within housing 14 and having an arm member 40 connected to half-nut 32. In accordance with the invention, four levers 38 (See FIG. 8) are included so as to provide stable operation. Of course, other types and numbers of levers may be used in accordance with the invention.

FIG. 4 illustrates a side view of a lever member 38 for use with the present invention. Lever 38 preferably has arm 40 and an additional arm 44, and arms 40, 44 are preferably joined at a pivot point 46 so as to define a substantially L-shaped lever. As shown, lever 38 preferably has one or more holes which may be used for attachment to the other elements of lever structure 36 as desired and as will be described below. Levers 38 are preferably pivotally mounted to a carriage member 42 (FIGS. 5–6) which is disposed within housing 12. Lever 38 is preferably pivotably mounted at pivot point 46 to carriage 42.

A trigger member 48 is preferably mounted within housing 12, with arms 44 of levers 38 connected thereto. Trigger member 48 is movable or slidable so as to pivot levers 38 as desired. FIG. 1 illustrates a slidable trigger member 48 in a forward, non-depressed position. In this position, in accordance with the invention, half-nut 32 is engaged with rod 22 as shown. Rearward depression of trigger member 48 in the direction of arrow A as shown in FIG. 1 in accordance with the invention causes pivot of levers 38 around pivot point 46 so as to cause arms 40 of levers 38 to positively disengage half-nut 32 from rod 22. In this way, depression of trigger 48 advantageously is operative to rapidly and positively disengage half-nut 32 from rod 22 as desired.

Trigger 48 may be any suitable structure properly positioned for operation so as to pivot levers 38 in accordance with the invention. FIG. 7 illustrates an example of a simple trigger 48 for use with the present invention. As shown, trigger 48 has pins 58 for pivotable connection to levers 38. Trigger 48 may also preferably have a profiled surface 49 exposed exterior of housing 12 so as to facilitate use thereof. Returning to FIG. 1, trigger 48 may be freely positioned within housing 12 and held in place therein by levers 38. Alternatively, trigger 48 could be slidably mounted within housing 12.

As shown in FIGS. 1 and 4, the arm 44 of lever 38 which is acted on by trigger 48 is preferably longer than arm 40 so that less force on trigger 48 is required to disengage half-nut 32. In this way, advantageously, half-nut 32 and rod 22 may be securely threadedly engaged against rearward slippage and nevertheless remain substantially disengagable in a rapid and convenient manner should the need for such rapid disengagement arise.

Trigger 48 is preferably biased forward toward the engaged position by any suitable biasing member such as spring 50 or the like. Spring 50 is preferably selected so as to provide a biasing force against trigger 48 which is sufficient to re-engage half-nut 32 with rod 22 when trigger 48 is released. Spring 50 is also preferably selected having a biasing force which is sufficiently small that forward ratchet of rod 22 in half-nut 32 is possible when half-nut 32 and rod 22 are engaged. Spring 50 may preferably be arranged between a suitable portion of housing 12 and pin 51 on trigger 48.

Trigger 48 may be slidably or otherwise movably disposed in housing 12 in any desired fashion. Further, as mentioned above, levers 38 may preferably be pivotably connected as desired to half-nut 32, carriage 42, and trigger 48 through pin and hole structures. In this regard, and as shown in FIG. 4, levers 38 are preferably provided with holes 52 in the proper positions, which holes mate with pins 54 on half-nut 32 (FIG. 2), with pins 56 on carriage 42 (FIGS. 5–6), and pins 58 on trigger member 48 (FIG. 7). Matching holes and pins in accordance with the invention are also indicated in FIG. 8.

Pivotable connection of lever 38 to both trigger 48 and half-nut 32 provide for positive engagement and disengagement of half-nut 32 from rod 22 in accordance with the present invention. When trigger 48 is depressed, levers 38 are pivoted and arms 40 connected to half-nut 32 positively downwardly displace half-nut 32 so as to disengage same from rod 22. When trigger 48 is released, biasing member or spring 50 returns trigger 48 to the forward, non-displaced position which pivots levers 38 back to the initial starting position so that arms 40 of levers 38 positively re-engage half-nut 32 with rod 22.

In further accordance with the invention, it is desirable to provide convenient means for pulsing plunger 20 forward and backward in relatively small increments so as to provide slight inflation and deflation or pulsing of the balloon catheter to which syringe assembly 10 is connected. With conventional apparatus, this would be possible only by rotating knob 28 clockwise and counter-clockwise in rapid succession and thereby displacing plunger 20. Such rapid changes in direction of rotation of knob 28 are fatiguing to the hand and wrist of the surgeon. In accordance with the invention, means are provided for pulsing the entire rod plus threaded engagement structure so as to provide the desired pulsing without disengaging rod 22. This advantageously provides pulsing of plunger 20 with rod 22 and nut 32 engaged by simple, repeated squeezes of the hand.

In accordance with the invention, pulsation of plunger 20 is provided by slidably mounting or positioning carriage 42 within housing 12, and by providing means for pulsing carriage 42 forward and backward in the desired increment.

FIGS. 5 and 6 illustrate carriage member 42 in accordance with the invention. As shown, carriage 42 may suitably have a substantially yoke-like structure, with pins 56 for engagement with levers 38 being inwardly directed. In this configuration, carriage 42 has a smooth side wall on each side thereof so as to facilitate slidable mounting of carriage 42 within housing 12. This may be accomplished by providing suitable tracks within housing 12 in which carriage 42 is slidable.

Referring back to FIG. 1, an additional trigger member 60 may be provided in accordance with the invention for pulsing carriage 42. As shown, trigger 60 may preferably be pivotably mounted to a rear portion of pistol grip 16, for example at a hinge pin structure 61, so that trigger 60 may be operated independently of trigger member 48. As shown, trigger 60 may suitably comprise an elongated lever member which is pivotably mounted within housing 12 so as to contact carriage 42. Biasing means 62 may suitably be provided so as to bias trigger 60 into a non-pulsed position. When it is desired to pulse plunger 20 within housing 12, a repeated squeezing and releasing of trigger 60 will pulse carriage 42 plus the engaged rod 22 and plunger 20 within housing 12 as desired. As shown in FIG. 1, trigger 60 need not be connected to carriage 42 as pressure within the balloon catheter and barrel 14 to the pressure side of plunger 20 will serve to force plunger 20, rod 22, threaded member 26 and carriage 42 back toward the non-pulsed starting position when trigger member 60 is released.

It should be noted that the typical use for which syringe assembly 10 is made is to provide pressurized fluid for inflating balloon catheters for one or another type of treatment to be administered to a patient. One such treatment is to compress various types of obstructions in an artery wall outwardly so as to widen the passage of the artery to permit sufficient flow of blood. This is accomplished by inflating the balloon catheter at the obstructed portion of the artery. A useful technique for use during such treatment is to pulse the balloon at the point of treatment so as to more effectively compress obstructive material outwardly of the artery. The aforedescribed pulsing of plunger 20 within barrel 14 renders the desired pulsing available without risk of backward slippage or other undesirable disengagement of rod 22 because rod 22 and nut 32 are not disengaged during pulsing.

It is apparent that there has been provided in accordance with this invention a syringe assembly which fully satisfies the objects, means, and advantages set forth hereinbefore. While the invention has been described in combination with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

What is claimed is:

1. A syringe assembly, comprising:

a housing having a barrel having a forward fluid discharge end;

a plunger disposed within said barrel and having a threaded rod extending therefrom;

threaded means for engaging said threaded rod for threaded advancement of said plunger relative to said barrel;

control means for positively engaging and positively disengaging said threaded means with said threaded rod, said control means having a first arm member and a second arm member, said first arm member being pivotably connected to said threaded means, said control means being pivotably mounted for pivot between an engaged position wherein said first arm member positively engages said threaded means with said threaded rod, and a disengaged position wherein said first arm member positively disengages said threaded means from said threaded rod; and trigger means mounted relative to said housing and pivotably connected to said control means for pivoting said control means toward said disengaged position.

2. A syringe assembly according to claim 1, further comprising means for biasing said control means toward said engaged position.

3. A syringe assembly according to claim 1, wherein said second arm is longer than said first arm.

4. A syringe assembly according to claim 1, further comprising biasing means for exerting a biasing force on said trigger means so as to bias said control means toward said engaged position.

5. A syringe assembly according to claim 1, wherein said threaded rod has threads which are deflected rearwardly and said threaded means comprises a threaded nut element having threads which are deflected forwardly whereby, when said threaded means is engaged with said threaded rod, said threaded rod is ratchetable in a forward direction relative to said nut element, and is locked against ratchet in a rearward direction relative to said nut element.

6. A syringe assembly according to claim 1, wherein said threaded rod extends exterior of said housing so as to provide means for rotating said threaded rod relative to said threaded means.

7. A syringe assembly, comprising:

a housing having a barrel having a forward fluid discharge end;

a plunger disposed within said barrel;

means for advancing said plunger forward relative to said barrel; and pulsing means for pulsing said plunger in said barrel from a starting position to a forward pulsed position wherein said plunger is displaced forwardly from said starting position and from said forward pulsed position to said starting position whereby fluid is pulsed out of and into said barrel through said forward fluid discharge end, wherein said plunger further includes a threaded rod attached to said plunger and said means for advancing includes threaded means for engaging said threaded rod for threaded advancement, wherein said pulsing means pulses said threaded means and wherein said threaded means is directly engaged with said threaded rod during pulsing from said starting position to said forward pulsed position and from said forward pulsed position to said starting position.

8. A syringe assembly according to claim 7, wherein said pulsing means comprises means for sliding said plunger back and forth between said starting position and said forward pulsed position.

9. A syringe assembly according to claim 8, wherein said means for sliding comprises a trigger member positionably mounted relative to said housing and contacting at least one of said plunger and said means for advancing, said trigger member being positionable for pulsing said plunger between said starting position and said forward pulsed position.

10. A syringe assembly according to claim 9, further comprising means for biasing said trigger member to a position corresponding to said starting position of said plunger.

11. A syringe assembly according to claim 7, wherein said threaded rod is longitudinally slidable relative to said barrel toward and away from said fluid discharge end, and wherein said threaded means is longitudinally slidable relative to said barrel toward and away from said fluid discharge end, and wherein said threaded means directly engages said threaded rod during sliding toward and away from said fluid discharge end.

12. A syringe assembly, comprising:

a housing having a barrel having a forward fluid discharge end;

a plunger disposed within said barrel and having a threaded rod extending therefrom;

threaded means for engaging said threaded rod for threaded advancement of said plunger relative to said barrel;

control means for positively engaging and positively disengaging said threaded means with said threaded rod; and means for pulsing said threaded means from a starting position to a pulsed position forward of said starting position, and from said pulsed position to said starting position while said threaded means is positively engaged with said threaded rod whereby said plunger is pulsed forward and rearward in said barrel.

13. A syringe assembly, comprising:

a housing having a barrel having a forward fluid discharge end;

a plunger disposed within said barrel and having a threaded rod extending therefrom;

threaded means for engaging said threaded rod for threaded advancement of said plunger relative to said barrel;

control means for positively engaging and positively disengaging said threaded means with said threaded rod, said control means having a first arm member and a second arm member, said first arm member being connected to said threaded means, said control means being pivotably mounted for pivot between an engaged position wherein said first arm member positively engages said threaded means with said threaded rod, and a disengaged position wherein said first arm member positively disengages said threaded means from said threaded rod; and trigger means mounted relative to said housing for pivoting said control means toward said disengaged position, said second arm member being connected to said trigger means, said first arm and said second arm of said control means being joined at a pivot point so as to define a substantially L-shaped lever, and wherein said lever is pivotably mounted within said housing at said pivot point.

14. A syringe assembly according to claim 13, further comprising a carriage slidably disposed within said housing, and wherein said lever is pivotably mounted at said pivot point to said carriage, and wherein said syringe assembly further comprises means for displacing said carriage within said housing so as to provide pulsating motion of said plunger in said barrel.

15. A syringe assembly according to claim 14, wherein said means for displacing comprises an additional trigger member movably mounted to said housing and contacting said carriage, said additional trigger member being movable between a pulsed position wherein said plunger is pulsed forward in said housing from a starting position, and a non-pulsed position wherein said plunger is returned to said starting position.

16. A syringe assembly according to claim 15, further comprising means for biasing said additional trigger member toward said non-pulsed position.

17. A syringe assembly according to claim 15, wherein said housing has a downwardly depending grip portion, and wherein said additional trigger member has a downwardly depending handle member and is pivotably mounted relative to said grip portion whereby squeezing said handle toward said grip portion pulses said plunger forward in said housing.

18. A syringe assembly according to claim 17, wherein said grip portion has a forward edge and a rearward edge, and wherein said trigger member is positioned at said forward edge and said additional trigger member is positioned at said rearward edge.

* * * * *